United States Patent [19]

Vlock

[11] 4,345,899

[45] Aug. 24, 1982

[54] DENTAL TWIST DRILL

[76] Inventor: David G. Vlock, 2 E. 65th St., New York, N.Y. 10021

[21] Appl. No.: 203,777

[22] Filed: Nov. 3, 1980

Related U.S. Application Data

[63] Continuation-in-part of Ser. No. 56,760, Jul. 12, 1979, abandoned.

[51] Int. Cl.$^3$ .............................................. A61C 3/02
[52] U.S. Cl. ................................... 433/165; 408/226
[58] Field of Search ............... 433/165, 102, 224, 220, 433/221; 408/223, 224, 225, 229, 230, 226

[56] References Cited

U.S. PATENT DOCUMENTS

| | | | |
|---|---|---|---|
| 362,934 | 5/1887 | Champion | 408/224 |
| 1,366,877 | 1/1921 | Craig | 433/102 |
| 1,643,679 | 9/1927 | Roderick | 408/225 |
| 2,264,922 | 12/1941 | Van Hooser | 408/224 |
| 2,715,772 | 8/1955 | Fritz | 433/165 |
| 3,564,948 | 2/1971 | Pomernacki | 408/226 |
| 3,832,779 | 9/1974 | Reynaud | 433/165 |
| 4,050,345 | 9/1977 | Reibetanz et al. | 408/226 |

FOREIGN PATENT DOCUMENTS 669186  11/1929  France ............................... 408/226

OTHER PUBLICATIONS

"Power Drill and Sanding Accessories", p. 813 of Montgomery Ward's Catalog, Fall and Winter 1978.

*Primary Examiner*—Gene Mancene
*Assistant Examiner*—John J. Wilson
*Attorney, Agent, or Firm*—Lawrence Rosen

[57] ABSTRACT

A dental twist drill including a cutting section consisting of blades extending at an angle to the main axis of the drill. These cutting blades are carried at the end of helically arranged bearing surfaces which extend parallel to the main axis of the drill and thereby furnish, when rotating, a cylindrical support for the cutting section against the sides of the post hole being drilled. The outer bearing surfaces are separated by flutes. These flutes convey the debris axially along the drill, away from the direction of drilling into a recess or chip trap. A further bushing or bearing surface having the same outer diameter as the first mentioned bearing surface and hence a diameter equal to the interior diameter of the post hole being drilled is connected to the recessed section, and preferably this bushing is also formed of a plurality of helically arranged bearing surfaces alternated with flutes. The outer surfaces of the bearing surface match the post hole exactly. The flutes serve to convey the debris further away from the cutting site and out through the top of the hole being drilled.

8 Claims, 7 Drawing Figures

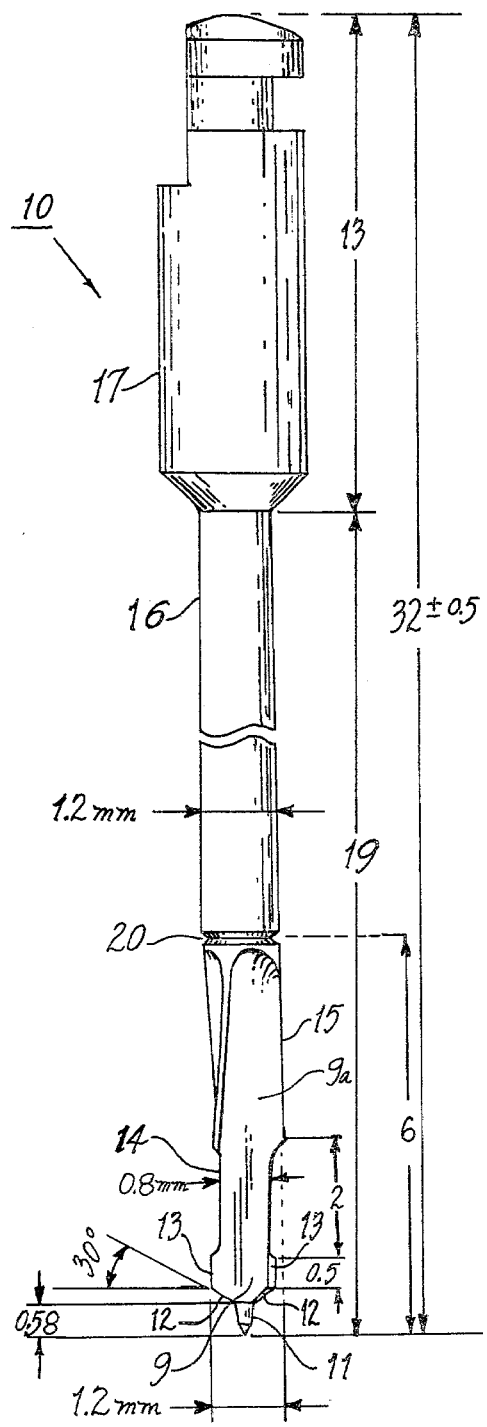
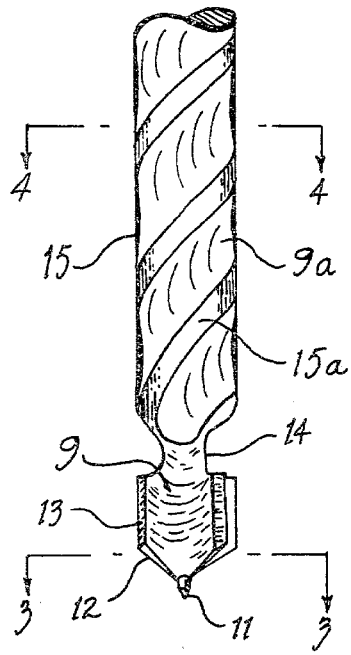
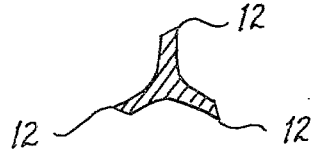
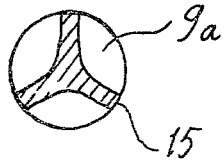

DENTAL TWIST DRILL

The present invention is a continuation-in-part of the invention described in application Ser. No. 56,760, filed July 12, 1979 now abandoned.

BACKGROUND OF THE INVENTION

The present invention relates to dental twist drills and more particularly to dental twist drills of the type utilized in conjunction with the anchoring of prefabricated post cores in the tooth canal.

In root canal therapy it is customary to drill a relatively deep hole into the root of the tooth for reception of a post core or anchor therein, the anchor or post core to be subsequently surmounted by a crown. In formation of the deep hole it is extremely important to maintain the side walls of the canal as parallel as possible to insure optimum securement of the post core therein. However, it is commonplace, during drilling of the canal, for the resultant hole to be tapered and for an undesirable enlargement of the opening of the canal to develop. Generally these effects are attributable to movement of the hand of the operator or to wobbling of the handpiece which drives the drill. Systems currently in use employ prefabricated post cores or anchors which are size-correlated with the drill used to form the canal. The post core or anchor achieves retention by virtue of a friction-fit or by a screw thread adjacent to the top of the canal opening. It will thus be appreciated that when a tapered hole is formed the bite of the screw threads into the tooth structure is decreased with consequent diminution of retention of the post core within the canal. In such instances cement is frequently resorted to in an attempt to maximize retention; however, the cement is susceptible to fracture and pulverization which results in loosening of the post core and crown.

One system for the anchoring of prefabricated metal posts into the roots of teeth employing anchors having parallel side walls sized precisely to the diameter of a corresponding uniform diameter twist drill is marketed by Star Dental Mfg. Co., Inc. of Conshohocken, Pennsylvania. Such system is known as the Star Dental Radix-Anchor System. As stated earlier, optimum securement of the Radix-Anchor is enhanced by formation of a parallel-sided canal.

SUMMARY OF THE INVENTION

It is one object of the invention is to provide a dental twist drill having a cutting section and bushing section arranged thereon so as to enable the formation of a parallel-sided cylindrical deep hole in a tooth.

It is another object of the invention to provide a dental twist drill specially constructed to enable formation of a parallel-sided cylindrical deep hole in a tooth and to accommodate the debris produced so as not to interfere with or adversely affect such hole formation.

It is yet another object of the invention to provide a dental twist drill of the character described which can be size-correlated with a prefabricated anchor or post core to optimize retention of the anchor or post core in the canal formed by the drill.

In accordance with the present invention there is provided a dental twist drill having a cutting section of predetermined uniform diameter. The cutting section is preferably a tripartite blade set at an appropriate cutting angle so that when subjected to downward pressure and operated at a substantial speed as a twist drill it will cut away the material immediately below the blade. The blade elements extend radially from a pilot point at an appropriate cutting angle of the order of 30° from a plane transverse through the opening of the hole which is to be drilled for the post. The blades are connected to a plurality of bearing surfaces, the outer boundaries of which exactly match the diametric size of the opening which is to be drilled for reception of the post. Therefore, immediately upon entry of the blades into the tooth they are guided and supported by bearing surfaces which extend from the cutting blades and are in circumferential contact with the interior of the opening which is being drilled. Hence, lateral support is immediately provided for the drill as soon as it creates an opening in the outer surface of the tooth just distal to the drilling point.

The support for the drill is thus provided by the helical bearing surfaces which extend parallel to the axis of the drill and therefore are guided by the opening which has just been formed preventing wobble of the drill and consequential distortion of the perfectly cylindrical hole. Since the flutes are helical, they are utilized to provide a means for conveying the debris resulting from the cutting surfaces, distally away from the cutting area. This debris is delivered to a recessed portion just distal to the first section of the bearing. The recessed portion provides a place for the debris to be deposited without interfering with the cutting action and without presenting any additional material at the sides of the drill which will interfere with drilling an accurate post hole.

Since the drill must provide a straight opening in the area of the root canal, further wobble of the drill can be prevented by a further extension of the drill, distal to the recess previously referred to, which extension also has exactly the same outside diameter as the inside diameter of the hole being drilled so that the sides of the opening in the tooth support the drill against wobble. This further part may also be provided with, or formed by a series of somewhat helical edges which are not cutting edges but are simply substantially smooth edges which will bear against the side of the hole in the tooth and thereby support the drill, preventing lateral movement. The utilization of helical flutes between each bearing surface is again to provide a means for conveying debris from the recess just distal to the first bearing surface and to convey the debris out of the hole.

The drill itself may be appropriately marked or sized so that the progress of the drilling may be observed by the dentist and halted when a bench mark on the drill has reached a position in registry with the outer surface of the tooth. In addition, appropriate stops may be placed on the drill shank.

Thus the primary object of the present invention is the provision of a twist drill for drilling a perfectly straight non-tapered, non-conical but cylindrical opening in a tooth to receive a post wherein the cutting edge of the drill is connected to bearing surface which bear against the side of the opening already drilled in order to provide support for the drill so that it will not wobble.

A further object of the present invention is the provision of a debris trap just beyond or distal to the first bearing surface connected to the blades so that debris carried by the rotation of the fluted side portions will have a place to be deposited.

A further object of the present invention is the utilization of a further section or support for the drill again having an outer diameter equal to the inner diameter of the hole being drilled where preferably this additional section also is provided with flutes for carrying debris away from the debris trap.

All of these various objects refer back to the principal object of the present invention which is to drill an opening which is perfectly cylindrical, not conical or tapered in any way as a result of any possible lateral movement of the drill without requiring any special tools.

The foregoing and many other objects of the present invention will become apparent in the following description and drawings in which:

BRIEF DESCRIPTION OF THE DRAWINGS

FIG. 1 is a plan view of the novel drill of the present invention.

FIG. 2 is a view in perspective of the cutting section of the drill of FIG. 1.

FIG. 3 is a cross-sectional view taken on line 3—3 of FIG. 2 looking in the direction of the arrows.

FIG. 4 is a cross-sectional view taken on line 4—4 of FIG. 2 looking in the direction of the arrows.

DESCRIPTION OF THE PREFERRED EMBODIMENTS

Figure 7:
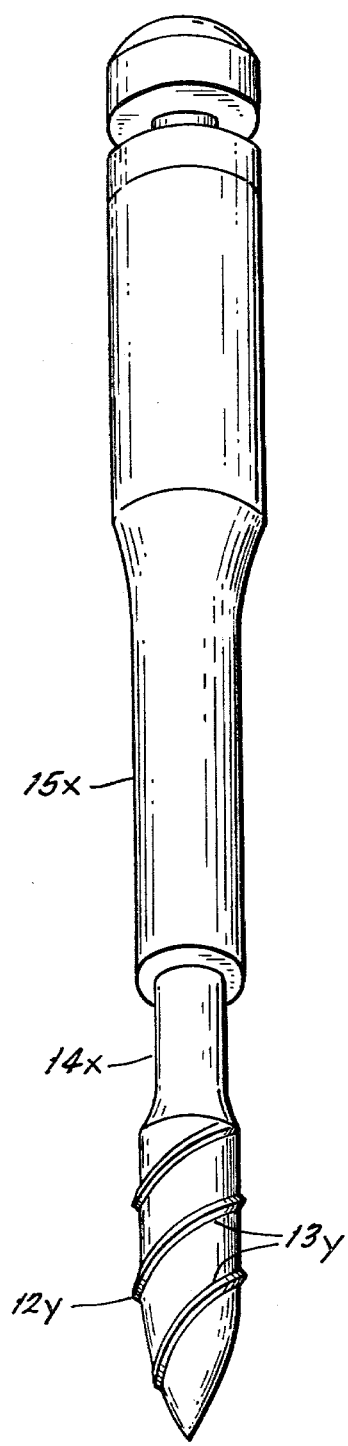
FIG. 7 is an elevation of another modified form of the drill of the present invention which, however, is a preliminary model, the FIG. 1 form being preferred.

Before explaining the invention in detail it is to be understood that the invention is not limited in its application to the details of construction and to the arrangement of parts illustrated in the drawings since the invention is capable of other embodiments and of being practiced or carried out in various ways. It is to be further understood that the phraseology or terminology employed is for the purpose of description only and not by way of limitation.

Referring first to FIGS. 1–4, the drill 10 comprises a plurality of sections including the pilot point 11, the cutting blades 12, 12 (preferably three in number), the bearing surfaces or bushing guide 13 which carry the cutting blades 12 at the lower end of each thereof, the debris collecting recess 14, the second guide bushing 15, the support post 16 and the section 17 which may be interengaged with the drill chuck mechanism.

Dimensions shown in FIG. 1 not for the purpose of limiting the particular disclosure to the dimensions themselves, but to illustrate the relationship among the parts. Thus, the cutting blades 12 at the end of the bearing surfaces 13 are preferably at an appropriate radial angle for assisting and creating an opening and cutting at the bottom of the opening. In this case the cutting angle is shown as preferably of the order of 30° from a plane transverse through the opening which is being created.

In order to provide immediate relief and support for the drill 10, as the cut is being made, the cutting blades 12 are supported by the bearing surfaces 13. Flutes 9 are somewhat helically arranged on the drill 10 so that they will serve as a conveyor for the cutting debris.

The most important aspect of the bearing surfaces 13, however, is that they have outer surfaces which are exactly parallel to the main axis of the drill 10 and are dimensioned, with respect to the cutting blades 12, so that the sides of the bearing surfaces 13 will bear against the inner surface of the opening which has been drilled by the blades 12. This provides support for the blades 12 and for the entire drill 10 to prevent wobble from occurring.

Figure 6:
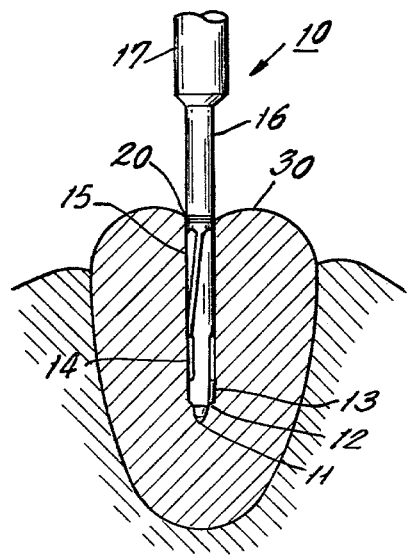
FIG. 6 is a view showing the drill of FIG. 1 operating within a tooth.

When the drill is initially inserted and positioned at the tooth surface as shown in FIG. 6, the initial cut which is made by the blades 12 makes the initial portion of the opening. As soon as the opening begins to be formed the drill is supported by the sides of the opening owing to the fact that the sides of the bearing surfaces 13 are exactly parallel to the sides of the opening; unintentional wobble is prevented and the hole which is drilled is completely cylindrical.

Since there must be some means for extracting the debris while the drill is being operated at high speed, then instead of having a solid section at the bushing area 13 which would furnish the support required, the utilization of the somewhat helically arranged flutes provides a means for conveying the debris away from the drilling site thereby preventing the formation of additional grinding material which might interfere with the proper operation of the drill. Thus the bearing surfaces 13 and flutes 9 serve the primary purpose of supporting the drill in the opening to prevent wobble and at the same time provide for the removal of debris, respectively.

A recess 14 is provided just above the bearing surfaces 13 so that a pocket will be created in which the debris may be deposited. The dentist has the option from time to time of removing the drill and removing the debris from the pocket 14. But with the type of high speed, water or otherwise cooled, drill which is used, it may not be necessary to halt the operation provided the debris can be further removed from the pocket at 14.

For this purpose, the bushing 15 is provided which has sides exactly matching the diameter and inner contour of the hole which is being drilled. The bushing section 15 is provided with a series of flutes 9a which act as a conveyor for removing debris away from the debris pocket 14 as the debris pocket 14 tends to fill so that the drill operation may continue in one substantially continuous motion without the necessity for removing the drill.

This is particularly so where the drill is initially formed in such a manner that the dentist is provided with indicia as to the depth of operation of the drill as, for instance, the recess 20 which may provide an indication of the depth to which the drill has been inserted into the tooth.

The dentist himself may provide such additional markings as he may desire or deem appropriate on the section 16 of the drill to indicate the position of the cutting edges 12 beyond the surface of the tooth and to guide himself accordingly.

However, the dimensions shown of the order of 6 mm from the cutting blade to the bench mark 20 may well be the average desirable dimension for the initial drilling of the post hole.

It should be kept in mind here that the primary function of the structure thus shown, including the utilization of the bearing surfaces 13 the edges of which are parallel to the main axis of the drill, and the section 15 having bearing surfaces 15a the edges of which are parallel to the main axis of the drill is to create a structure at both sections 13 and 15 which is intended to be exactly a match for the inner contour of the post hole which is being drilled. The utilization of this kind of structure for the drill itself thereby makes it unnecessary to use complex centering devices in order to hold the drill in perfect alignment since the drill creates its own perfect alignment when it enters the tooth surface.

It will be noted that the pilot tip 11 is of the order of ½ mm in length in order to provide a centering device to start the opening. The initial guide section 13 just above the cutting blades is shown as of the order of a ½ mm in length while the recess 14 for debris is shown of the order of 2 mm in length being contracted from a diameter of 1.2 mm to a diameter of 0.8 mm. These are only representative figures to show the general proportions. The essential element is that the guide bearing surfaces 13 are parallel to the axis of the drill and define a diameter exactly equal to the inner diameter of the hole to be drilled and that the same is true of the guide bearing surfaces 15a.

Figure 5:
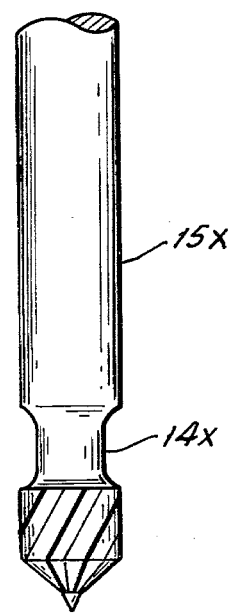
FIG. 5 is a partial plan view of a modified form of the drill of the present invention.

In FIG. 5 a modified form has been shown which is believed not to have all of the advantages of the structure shown in FIG. 1 in that the bushing section 15x, is shown without flutes and the debris trap area 14x is shown as inwardly curved at its upper and lower edges. Such inward curvature in view of the type of structure provided and the dimensions used is not believed, however, to be essential. It should be pointed out that the section 15 preferably should consist of a plurality of helical bearing surfaces and flutes defining a specific outer diameter matching the inner diameter of the hole in the tooth, and ensuring complete removal of all debris.

In FIG. 6 the drill of FIG. 1 has been shown entering the tooth 30 generally along the root canal area thereof in order to create the post hole as previously described. In this case the bench mark 20 has been shown as having reached the outer surface of the tooth indicating that the drill should stop.

FIG. 7 is a showing of a modified form of which the FIG. 1 structure is believed to be a distinct improvement. In the FIG. 7 structure the bearing surfaces 13y are provided with cutting edges 12y so that this structure which removes the debris and the cutting edges are the same. While such a device as shown in FIG. 7 is novel and feasible it does not produce the same kind of perfectly controlled cutting as is produced by the utilization of the structure of FIG. 1. Since it does not provide the guide tip 11 of FIG. 1, the angularly arranged blades 12y of FIG. 7 seek to combine the function of both the blades and guiding flutes in one element which is not believed to be as useful or desirable as the preferred structure of FIG. 1. The debris recess 14x is provided between the members 12y and the bushing section 15x. However, the bushing section 15x is here shown without the debris removing guiding flutes which it is believed as shown in connection with FIG. 1 are preferred.

While certain dimensions have been shown in connection with the structure of FIG. 1, it is obvious that the primary function of the device is the provision of a twist drill which will cut into a hole and, just as the hole is made will itself provide means for supporting the drill coaxially in the hole utilizing the side of the drill and the side of the hole for mutual support, thereby obviating the need for special tools and face clamps to ensure an absolutely non-conical hole and preventing any wobble from occurring owing to possible disturbance of the dentist's hand during the process of drilling.

From the foregoing it will be seen that a dental twist drill has been provided which is particularly well suited for use after root canal therapy where the formation of a parallel sided post hole is critical to the proper securement of the anchor or post core within the canal. The drill is, of course, also useful in other applications where similar criteria for a deep hole exist.

Although the invention has been described in specific terms it will be understood that various changes may be made in size, shape, materials and in the arrangement of the parts without departing from the spirit and scope of the invention as claimed.

What is claimed is:

1. A longitudinal dental twist drill comprising a plurality of cutting blades extending at an angle to the principal axis of the drill; a plurality of bearing surfaces supporting said cutting blades; said bearing surfaces extending helically along the drill; the outer bearing surfaces extending parallel to the main axis of the drill and defining, when rotated, a cylindrical surface; a plurality of flutes separating said bearing surfaces; an additional bearing section extending along the main axis of the drill; and a recess between said additional bearing section and said first mentioned bearing surface, serving as a pocket for the reception of debris transferred from the cutting members by the flutes along the axis of said drill; whereby a parallel-sided cylindrical deep hole is formed in a tooth when drilled with said dental twist drill.

2. A dental twist drill according to claim 1, said additional bearing section also comprising a plurality of helically arranged bearing surfaces which extend and define a cylindrical wall parallel to the main axis of the drill and equal to the cylindrical wall defined by the first mentioned bearing surfaces; said second mentioned bearing surfaces also being separated by a plurality of flutes which act on rotation of the drill to transfer debris from said recess further along the axis of said drill.

3. The dental twist drill of claim 1, wherein a pilot point is provided axially of the end of said drill having said cutting blades and extending beyond said cutting blades.

4. The dental twist drill of claim 3, said cutting blades extending at an angle of 30° from a plane transverse to the main axis of said drill.

5. A dental twist drill of claim 4, said drill being adapted to form a non-tapered hole.

6. The dental twist drill of claim 5, wherein said first mentioned set of flutes extend axially for a distance of ½ mm and said recess for receiving debris extending axially for a distance of the order to 2 mm.

7. The dental twist drill of claim 6, having a bench mark on said drill at a distance from the cutting blades of said drill of the order of 6 mm from said cutting blades.

8. The dental twist drill of claim 2, wherein said mentioned second bearing section and set of flutes extend axially to transfer debris out of the hole.

* * * * *